United States Patent [19]

Fürstenwerth et al.

[11] Patent Number: 4,705,861
[45] Date of Patent: Nov. 10, 1987

[54] AMINOPHENYLBENZOTHIAZOLES

[75] Inventors: Hauke Fürstenwerth, Cologne; Karl H. Schündehütte, Leverkusen, both of Fed. Rep. of Germany

[73] Assignee: Bayer Aktiengesellschaft, Leverkusen, Fed. Rep. of Germany

[21] Appl. No.: 798,253

[22] Filed: Nov. 14, 1985

[30] Foreign Application Priority Data

Nov. 29, 1984 [DE] Fed. Rep. of Germany ....... 3443594

[51] Int. Cl.⁴ ........................................... C07D 277/66
[52] U.S. Cl. .................................. 548/178; 544/135; 544/368; 548/180
[58] Field of Search ................ 548/178, 180; 544/135, 544/368

[56] References Cited

U.S. PATENT DOCUMENTS

| 2,098,599 | 11/1937 | Shubert | 548/178 |
| 2,715,629 | 8/1955 | Zwilgmeyer | 548/178 |
| 2,733,242 | 1/1956 | Libby et al. | 548/178 |
| 3,274,171 | 9/1966 | Anderson et al. | 548/178 |
| 3,726,851 | 4/1973 | Litke | 548/178 |
| 3,972,875 | 8/1976 | Smith | 548/178 |
| 4,001,206 | 1/1977 | Schoefberger | 548/178 |

FOREIGN PATENT DOCUMENTS 1221937 2/1971 United Kingdom ............... 548/178

Primary Examiner—Mary E. Ceperley
Attorney, Agent, or Firm—Sprung Horn Kramer & Woods

[57] ABSTRACT

Benzothiazole derivatives of the formula

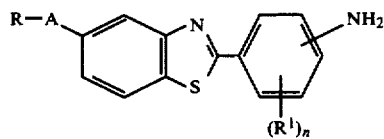

with the substituent meanings mentioned in the description, are starting compounds for the preparation of new azo dyestuffs. Some methods of preparing the new benzothiazole derivatives are described.

2 Claims, No Drawings

AMINOPHENYLBENZOTHIAZOLES

The invention relates to benzothiazole derivatives of the formula

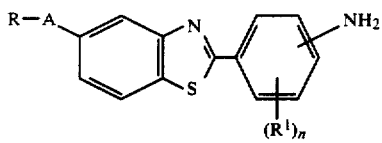

wherein

R = OH, OX, $NH_2$ NHX, $NX_2$, $NHSO_2X$
X = alkyl, alkenyl, cycloalkyl, aryl, aralkyl, or hetaryl,
$R^1$ = H, alkyl, alkoxy or halogen
A = $SO_2$ or CO and
n = 0, 1 or 2 it being possible for the abovementioned radicals to contain ionic or nonionic substituents customary in dyestuff chemistry, including in particular $SO^3H$ and COOH, to their preparation and to their use as intermediates for preparing dyestuffs.

Examples of suitable alkyl radicals are those having 1 to 12 C atoms.

Examples of suitable alkenyl radicals are those having 2 to 5 C atoms.

Suitable cycloalkyl radicals are in particular cyclopentyl and cyclohexyl.

Examples of suitable aralkyl radicals are $C_1$-$C_3$-alkylphenyl radicals which can be substituted in the phenyl nucleus, for example by Cl, $C_1$-$C_4$-alkyl or $C_1$-$C_4$-alkoxy.

Suitable aryl radicals are in particular phenyl radicals which can be substituted in corresponding manner.

Suitable hetaryl radicals are 5- or 6-membered quasi-aromatic N-, O- and/or S-containing heterocyclic ring systems.

Preferred compounds are those of the formula

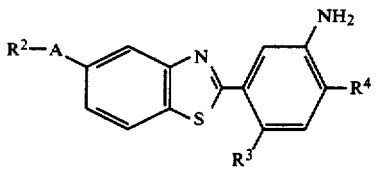

wherein
A = $SO_2$, CO
$R^2$ = $NR_5R_6$, OH, $NHSO_2R_5$
$R^3$ = H, $CH_3$, $OCH_3$, $OC_2H_5$, Cl
$R^4$ = H, $CH_3$, $OCH_3$, $OC_2H_5$, Cl
$R^5$, $R^6$ = hydrogen; a $C_1$-$C_8$-alkyl radical which is substituted by hydroxyl, amino, $C_1$-$C_4$-alkylamino, $C_1$-$C_4$-dialkylamino, $C_1$-$C_4$-trialkylammonium, halogen, cyano, $C_1$-$C_4$-alkoxy, carboxyl, aminocarbonyl or $C_1$-$C_4$-alkoxycarbonyl; a $C_2$-$C_4$-alkenyl radical; a cyclohexyl radical which is optionally substituted by $C_1$-$C_4$-alkyl; a phenyl, benzyl or phenylethyl radical which is optionally substituted by halogen, $C_1$-$C_4$-alkyl, $C_1$-$C_4$-dialkylamino, $C_1$-$C_4$-trialkylammonium or $C_1$-$C_4$-alkoxy; or a $C_1$-$C_4$-alkyloxycarbonyl, mono- or di-$C_1$-$C_4$-alklyaminocarbonyl, aminocarbonyl, mono- or di-$C_1$-$C_4$-alkylaminosulphonyl, 2-thienyl, 2-furyl, 2-tetrahydrofuryl, amino, $C_1$-$C_4$-alkylamino, di-($C_1$-$C_4$-alkyl)-amino or optionally $C_1$-$C_4$-alkyl- or $C_1$-$C_4$-alkoxy-substituted phenylamino or benzylamino radical, or $R^5$ and $R^6$, together with the N atom, form a 5- or 6-membered ring which optionally contains a further N or O atom.

Additionally preferred compounds are those of the formula

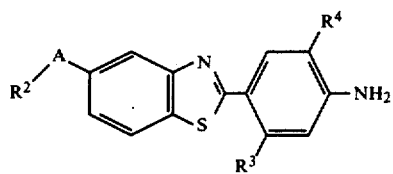

wherein
A, $R^2$, $R^3$ and $R^4$ have the meaning indicated in the formula II.

The invention also relates to a process for preparing the compounds (I), characterised in that 3- or 4-nitrobenzoyl chlorides of the formula

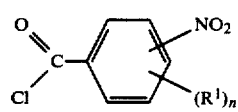

are reacted with 2-aminothiophenol derivatives of the formula

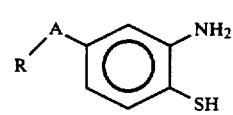

or with reaction products of 2-nitrohalogenobenzenes of the formula

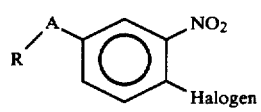

with sulphur alkali metal compounds (NaHS, $Na_2S$, $K_2S$); the intermediates—optionally without isolation—are cyclised and reduced or converted to compounds of the formula I; and the intermediates—if desired without isolation—are reduced and cyclised to compounds of the formula I.

In the formulae (IV) to (VI), R, R, $R^1$ and n have the meaning indicated in the formula (I) and Halogen stands for fluorine, chlorine or bromine.

The reductions are preferably carried out with sulphidic reducing agents. The cyclisations are preferably carried out under acid conditions, but can also be carried out under neutral or alkaline conditions.

The process according to the invention is carried out in detail by first converting a 3- or 4-nitrobenzoic acid of the general formulae VII with excess thionyl chloride or another acid-halogenating compound, such as phosgene, phosphorus trichloride, phosphorus pentachloride, or phosphorus oxychloride in a manner known per se (cf. Houben-Weyl, Methoden der Organischen Chemie [Methods of Organic Chemistry], 4th edition, volume 8, page 467 (1952); German Reich Pat. No. 1,026,750) into the corresponding 3- or 4-nitrobenzoyl chlorides of the general formula IV:

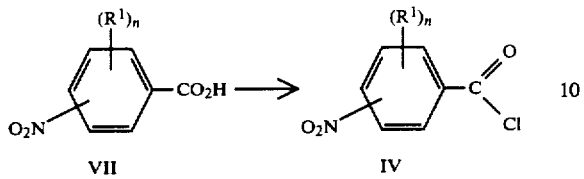

This reaction is generally carried out in the presence of small amounts of an organic nitrogen compound as a catalyst, preferably in the presence of dimethylformamide or pyridine, and at rising temperature, preferably from 20° to 100° C. The reaction of the 3- or 4-nitrobenzoic acid VII to the corresponding 3- or 4-nitrobenzoyl chloride IV is preferably carried out in the absence of a solvent, but it can also be carried out in inert organic solvents, for example methylene chloride, chloroform, carbon tetrachloride, dichloroethane, trichloroethane, n-hexane, cyclohexane, toluene, xylene, monochlorobenzene or o-dichlorobenzene.

The resulting melt or solution of the 3- or 4-nitrobenzoyl chloride (III) is—preferably without further purification—condensed with an aqueous suspension or solution of the aminothiophenol of the formula V.

The condensation reaction is normally carried out at pH 1-10, preferably 5-9, and at temperatures of from −10° to =100° C., preferably 50° to 80° C.

To maintain the optimal pH of 1 to 10, preferably 5 to 9, for the condensation reaction, it is possible to add, before or during the reaction, bases suitable for binding the hydrogen chloride which is liberated, for example sodium hydroxide, sodium carbonate, sodium hydrogencarbonate, sodium acetate, trisodium phosphate, disodium phosphate, monosodium phosphate, sodium formate or sodium propionate. The preferred solvent is water.

However, the aqueous reaction medium can also contain water-miscible solvents, for example alcohols such as methanol, ethanol or isopropanol, or non-water-miscible solvents, for example methylene chloride, chloroform, carbon tetrachloride, dichloroethane, tichloroethane, n-hexane, cyclohexane, toluene, xylene, monochlorobenzene or o-dichlorobenzene.

Furthermore, it is possible to add to the reaction medium used in the condensation reactions surfactants, for example an anionic surfactant, cationic surfactants, amphoteric surfactants or nonionic surfactants (cf. Ullmanns Enzyclopadie der technischen Chemie [Ullmann's Encyclopedia of Chemical Technology], volume 16, pages 724–748 (1965) or "Surface Activity" by J. L. Moilliet, B. Collie and Black, 2nd edition, chapters 10-15). The addition of surfactants raises the rate of reaction of the condensation reactions. The condensation reactions are normally complete at 50° C. to 80° C. within 1 to 6 hours.

The initial products in this condensation reaction are compounds of the formula

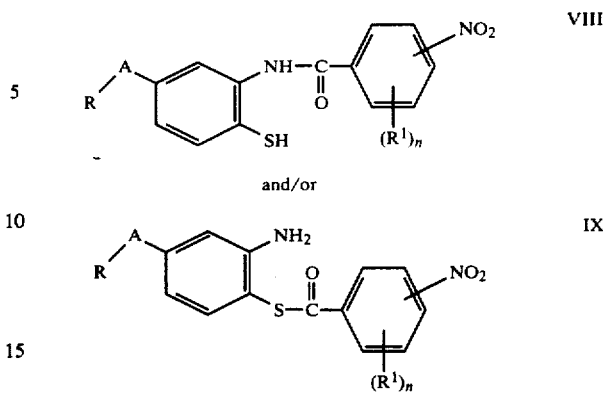

which are cyclised to benzothiazoles of the formula

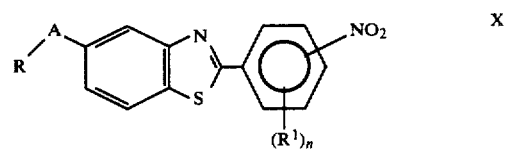

and are then reduced to benzothiazoles of the formula I.

The cyclisation of VIII and/or IX is preferably carried out at pH 0-5.

In a preferred embodiment of the present invention, the reaction steps of condensation, cyclisation and reduction are combined into a single process step.

In this preferred process variant (a), the condensation products of the formula IV are reduced with sulphidic reducing agents, such as, for example, hydrogen sulphide, alkali metal sulphides or alkali metal polysulphides, in particular with an alkali metal hydrogensulphide, for example of technically customary hydrosulphide solution (sodium hydrogensulphide).

In a particularly preferred embodiment of the present invention, the primary adducts VIII and/or IX are first reduced to the amino compounds

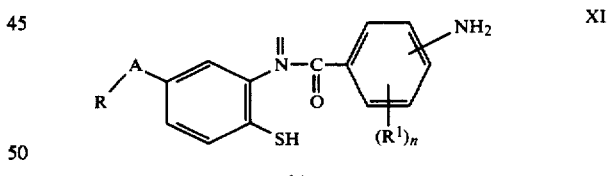

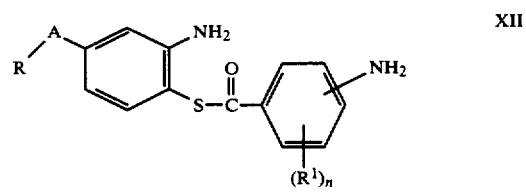

and these are then cyclised, preferably at pH 0-5, to give the benzothiazole derivatives of the formula I.

In this process variant the condensation products of the formula VIII/IX can likewise be converted without isolation of intermediates into the end products of the formula (I) using a so-called single-vessel method. In this method, the heterocyclic amines of he formula (I) are likewise obtained in excellent quality and in high yields, which is surprising in view of the process which proceeds via a plurality of stages without intermediate isolation and purification of the intermediate stages which occur.

In a very particularly preferred embodiment (b) of the present invention, nitrobenzoyl chlorides of the formula IV are made to react with reaction products of nitrohalogen compounds of the formula VI with sulphur alkali metal compounds. The products of reacting VI with sulphur alkali metal compounds are, depending on reaction conditions and substituents, aminotiophenols of the formula V and/or disulphides and polysulphides of the formula XIII (cf. German Offenlegungsschriften Nos. 2,127,989, 2,053,715 and 2,503,164; J. Mech. Chem. 14 248 et seq. (1971), Monatshefte f. Chem. 56 365 et seq. (1930)).

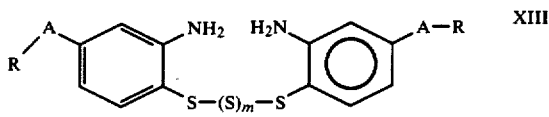

wherein
m can be=0 to 10, preferably 0 to 2.

It is surprising that not only mixtures of V and XIII but also XIII alone react or reacts with nitrobenzoyl chlorides of the formula IV with subsequent reduction and cyclisation on the one hand or cyclisation and reduction on the other in high yields and high purity to give benzothiazole derivatives of the formula I. In this very particularly preferred process variant, the reaction steps of reaction with sulphur alkali metal, reaction with nitrobenzoyl chlorides, reduction and cyclisation are combined into a single process step. The reduction-cyclisation or cyclisation-reduction of this process variant (b) are subject to the same remarks as process variants (a). In the formulae VII to XIII, A, R, R¹ and n have the meaning indicated in the formula I.

Nitrobenzoic acids of the formula VII, aminothiophenols of the formula V and nitrohalogenobenzenes of the formula VI are known, as are disulphides and polysulphides of the formula XIII, and/or can be prepared by methods described in the literature.

Examples of 3- or 4-nitrobenzoic acids (VII) which can be used for preparing the 3- or 4-nitrobenzoyl chlorides IV required for the condensation reaction are:

Table 1

4-Nitrobenzoic acid
2-Methyl-4-nitrobenzoic acid
3- Methyl-4-nitrobenzoic acid
3,5-Dimethyl-4-nitrobenzoic acid
2-Ethyl-4-nitrobenzoic acid
2-Methoxy-4-nitrobenzoic acid
3-Methoxy-4-nitrobenzoic acid
2,3-Oimethoxy-4-nitrobenzoic acid
3,5-Oimethoxy-4-nitrobenzoic acid
2-Methyl-5-methoxy-4-nitrobenzoic acid
3-Ethoxy-4-nitrobenzoic acid
3-Methyl-6-methoxy-4-nitrobenzoic acid
2-Chloro-4-nitrobenzoic acid
3-Chloro-4-nitrobenzoic acid
2-Bromo-4-nitrobenzoic acid
3-Bromo-4-nitrobenzoic acid
3-Nitrobenzoic acid
2-Methyl-3-nitrobenzoic acid
4-Methyl-3-nitrobenzoic acid
5-Methyl-3-nitrobenzoic acid
6-Methyl-3-nitrobenzoic acid
5-Ethyl-3-nitrobenzoic acid
2,4-Dimethyl-3-nitrobenzoic acid
4,6-Dimethyl-3-nitrobenzoic acid
2-Methoxy-3-nitrobenzoic acid
4-Methoxy-3-nitrobenzoic acid
6-Methoxy-3-nitrobenzoic acid
4-Ethoxy-3-nitrobenzoic acid
5-Methyl-6-methoxy-3-nitrobenzoic acid
4-Methoxy-5-methyl-3-nitrobenzoic acid
4-Methyl-6-methoxy-3-nitrobenzoic acid
5,6-Dimethoxy-3-nitrobenzoic acid
2,4-Dimethoxy-3-nitrobenzoic acid
2,5-Dimethoxy-3-nitrobenzoic acid
4,5-Dimethoxy-3-nitrobenzoic acid
2-Chloro-3-nitrobenzoic acid
4-Chloro-3-nitrobenzoic acid
5-Chloro-3-nitrobenzoic acid
6-Chloro-3-nitrobenzoic acid
2,5-Dichloro-3-nitrobenzoic acid
2,6-Dichloro-3-nitrobenzoic acid
4,6-Dichloro-3-nitrobenzoic acid
2-Bromo-3-nitrobenzoic acid
4-Bromo-3-nitrobenzoic acid
5-Bromo-3-nitrobenzoic acid
6-Bromo-3-nitrobenzoic acid
4,5-Dibromo-3-nitrobenzoic acid
3-Ethyl-4-nitrobenzoic acid
3-n-Butyl-4-nitrobenzoic acid
3-Ethoxy-4-nitrobenzoic acid
3-n-Butoxy-4-nitrobenzoic acid To prepare amines of the formula I in accordance with the invention, use is preferably made of such 3- and 4-nitrobenzoic acid derivatives of the formula VII in which R¹ is hydrogen, methyl, methoxy or chlorine.

Examples of aminothiophenols which can be used are those of Table 2 below.

TABLE 2

$$\text{structure V}$$

A = SO₂ or CO

R = OH, NH₂, NHCH₃, N(CH₃)₂, NH—C₃H₆—N(CH₃)₂,

NH—C₆H₅, NH—C₆H₄—NHCOOH₃,

N(H)—C₆H₄(NHCOOH₃), morpholine, N—C₂H₄OH piperazine,

N(iC₃H₇)₂, N(CH₃)-piperidine, N(C₂H₄OCH₃)₂,

TABLE 2-continued

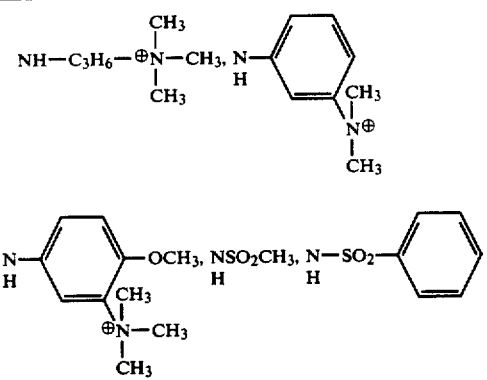

The nitrohalogenobenzenes of the formula VII used can be compounds in which A stands for CO or SO₂, R has the meanings indicated in Table 2 and Halogen stands for fluorine, chlorine or bromine.

The new compounds I, furthermore, are intermediates for the preparation of azo dyestuffs and can be diazotised in conventional manner and reacted with coupling components.

EXAMPLE 1

2-(4'-Aminophenyl)-benzothiazole-5-sulphonic acid 158 g of the sodium salt of 4-chloro-4-nitro benzene-sulphonic acid (technical, about 83% pure) are dissolved at about 80° C. in 400 ml of water. 180 ml of 30% strength aqueous sodium hydrogen sulphide solution (technical) are added dropwise in the course of about 30 minutes. The mixture is then stirred at 90° C. for one hour and is then cooled down to 70° C., and at at this temperature 93 g of 4-nitrobenzoyl chloride are added. The pH of the mixture is held at 8 by addition of sodium hydroxide solution. As soon as the pH remains constant, 180 ml of 30% strength aqueous sodium hydrogen sulphide solution are added, and the reaction mixture is boiled under reflux for one hour. The reaction mixture is then brought to pH 1 with hydrochloric acid and is boiled under reflux for 5 hours. After cooling down, the precipitated product is isolated. The crude product is heated to 90° C. in a mixture of 300 ml of water and 150 ml of 20% strength ammonia water. The mixture is filtered while still hot, and 50 g of sodium chloride are added to the filtrate while still hot. On cooling down, 125 g of pure product of the formula

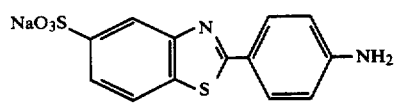

crystallise out.

NMR (DMSO) δ=3.40 (s, 2H), 6.70 (d, 2H), 7.65 (d, 1H), 7.78 (d, 2H), 7.95 (d, 1H), 8.12 (s, 1H).

EXAMPLE 2

158 g of sodium 4-chloro-3-nitrobenzenesulphonate are reacted with NaHS solution as described in the example. A solution of 93 g of nitrobenzoyl chloride in 130 ml of toluene is added at 70° C. pH 8 is maintained with sodium hydroxide solution. As soon as the pH of the mixture remains constant, 180 ml of 30% strength aqueous sodium hydrogensulphide solution are added. The reaction mixture is then heated to from 100° to 105° C., and the starting toluene is recovered by distillation. After the toluene has been distilled off, the mixture is brought to pH 1 with hydrochloric acid and is boiled under reflux for a further 3 hours. Isolation and separation from sulphur are carried out as in Example 1. The result obtained is 120 g of product which is identical to that of Example 1.

EXAMPLE 3

158 g of the sodium salt of 4-chloro-3-nitrobenzene-sulphonic acid (technical, about 83% pure) are dissolved at 80° C. in 400 ml of water. A solution of 130 g of Na₂S×3H₂O and 16 g of sulphur in 100 ml of water is added dropwise in such a way that the reaction mixture boils lightly under reflux. After this the mixture is boiled for a further 2 hours. The mixture is then reacted at 70° C. and pH 8 as described in Example 1 with 83 g of 4-nitrobenzoyl chloride, which is followed by reduction with 180 ml of 30% strength NaHS solution and cyclisation under acid conditions. Isolation and purification are carried out as described in Example 1. The result obtained is 90 g of product which is identical to that of Example 1.

EXAMPLE 4

93 g of 4-nitrobenzoyl chloride are added at 70° C. to 103 g of 2-aminothiophenol-4-sulphonic acid in 400 ml of water. pH 8 is maintained by addition of sodium hydroxide solution. As soon as the pH of the reaction mixture remains constant, 180 ml of 30% strength NaHS solution are added as in Example 1, which is followed by cyclisation under acid conditions and working up as described in Example 1. The result obtained is 135 g of product which is identical to that of Example 1.

EXAMPLE 5

158 g of the sodium salt of 4-chloro-3-nitrobenzene-sulphonic acid are reacted at pH 7.5 to 8.5 with NaHS solution and 4-nitrobenzoyl chloride as described in Example 1. As soon as the pH of the reaction mixture remains constant, the mixture is brough to pH 1 with HCL and is boiled under reflux for one hour. Cooling down is followed by isolation and washing with H₂O. The moist paste of the product of the formula

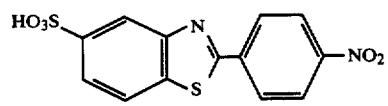

is suspended in 500 ml of water and, starting at 80° C., 180 ml of 30% strength NaHS solution are added. The mixture is boiled under reflux for 1 hour and is brought to pH 1 with hydrochloric acid, and the product is isolated. The crude product is heated to 90° C. in a solution of 20 g of NaOH in 500 ml of water, and is filtered, the filtrate is brought to pH 1 with HCL, and is stirred until cold, and the product is isolated, washed and dried. This gives 120 g of product of the formula

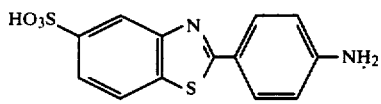

If the instructions of Examples 1 to 6 are followed using in place of 4-nitrobenzoyl chloride the acid chlorides of the nitrobenzoic acids listed in Table 1 of this application, this produces correspondingly substituted benzothiazole-5-sulphonic acid derivatives.

EXAMPLE 6

115 g of product of the formula

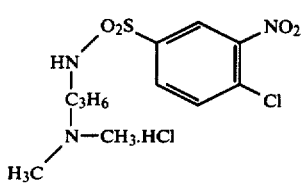

prepared from 4-chloro-3-nitrobenzenesulphonyl chloride and "Amin Z" [amine Z], are reacted in 300 ml of water with 20 g of sodium carbonate and 130 ml of 30% strength NaHS solution analogously to Example 1. At 75° C., 65 g of 4-nitrobenzoyl chloride are added, pH 8 is maintained with sodium hydroxide solution, stirring follows for 1 hour, 130 ml of 30% strength NaHS solution are then added, which is followed by boiling under reflux for 1 hour, adjustment to pH 1 with hydrochloric acid, boiling under reflux for 2 hours, cooling down, removal of precipitated sulphur by filtration and setting of filtrate at pH 11 with NaOH. The product initially appears in the form of an oil, but later, after stirring, in the form of crystals. Isolation and drying gives 80 g of product of the formula

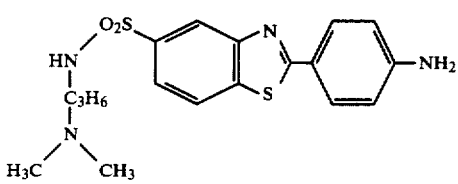

NMR (DMSO): 1.70 (m, 2H), 2.20 (s, 6H), 2.35 (t, 2H), 3.33 (m, 2H), 5.86 (s, 2H), 6.65 (d, 2H), 7.75 (m, 3H), 8.02 (d, 1H), 8.32 (s, 1H), 8.55 (s, 1H).

EXAMPLE 7

180 g of product of the formula

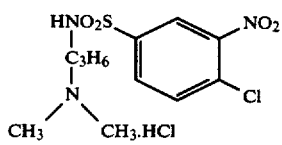

are reacted with 180 ml of 30% strength NaHS solution as described in Example 6. 110 g of 3-nitro-4-methoxybenzoyl chloride are then added at 70° C. and pH 8 is maintained with NaOH. As soon as the pH remains constant, the mixture is brought to pH 1 with HCl and is boiled under reflux for 2 hours. After cooling down, the product is isolated and recrystallised from DMF. This gives 110 g of the product of the formula

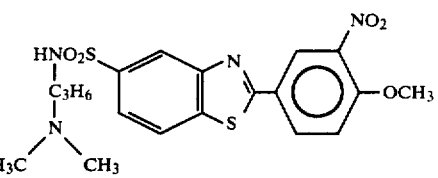

110 g of this product are reduced at 65° C. in 500 ml of ethanol with hydrogen in the presence of Raney nickel. Separation from the Raney nickel and isolation gives 80 g of product of the formula

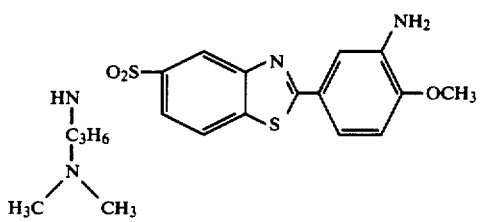

EXAMPLE 8

83 g of product of the formula

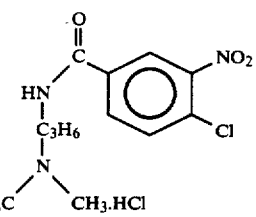

prepared from 4-chloro-3-nitrobenzoyl chloride and "Amin Z" [amine Z], are reacted in 300 ml of water with 25 g of sodium carbonate and 95 ml of 30% strength NaHS solution. analogously to Example 1. 55 g of 4-nitrobenzoyl chloride are then added at 70° C., pH 8 is maintained with sodium hydroxide solution, and boiling at reflux for 1 hour with 100 ml 30% strength NaHS solution is followed by setting of pH 1 with hydrochloric acid, boiling under reflux for a further 3 hours, cooling down, removal of precipitated sulphur by filtration, and setting of pH 11 with sodium hydroxide solution. The product initially appears in the form of an oil, but later, on stirring, in the form of crystals. Isolation and drying gives 75 g of product of the formula

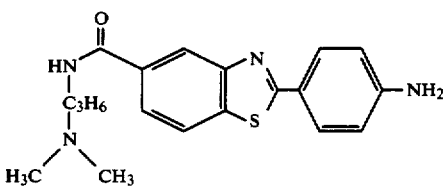

NMR (DMSO): 1.84 (m, 2H), 2.62 (s, 6H), 2.90 (m, 4H), 6.05 (s, 2H), 6.70 (d, 2H), 7.75 (3 H), 7.90 (s, 1H), 8.20 (d, 2H).

EXAMPLE 9

52 parts of 3-nitro-4-chlorobenzoic acid are dissolved at 80° C. in 200 parts of water and 10 parts of sodium hydroxide. 90 ml of 30% strength NaHS solution are added dropwise at 80°-85° C. in the course of 30 minutes. 44 parts of sodium dithionite are then added, which is followed by boiling under reflux for 2 hours. 47 parts of 4-nitrobenzoyl chloride are then added at 70° C., and pH 8 is maintained with sodium hydroxide solution. The mixture is stirred for 1 hour and 90 parts of 30% strength NaHS solution are then added. After one hour of refluxing the mixture is brought to pH 1 with hydrochloric acid and is boiled under reflux for a further 3 hours. After cooling down, the solids are isolated and washed with water. To separate off the sulphur, the moist crude product is suspended in 400 parts of water, the suspension is brought to a pH 10 with sodium hydroxide solution and heated to 90°-95° C., and the sulphur is filtered off. On cooling down, 55 parts of product of the formula

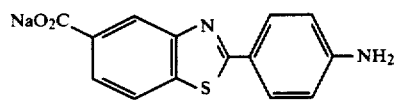

crystallise out.

NMR (DMSO): 5.80 (s, 2H), 6.62 (d, 2H), 7.68 (d, 2H), 7.85 (m, 2H), 8.30 (s, 1H).

EXAMPLES 10-15

The method of Example 1 is used to prepare:

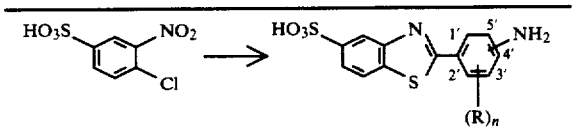

| Example | NH$_2$ | R |
|---|---|---|
| 10 | 4' | 3'-CH$_3$ |
| 11 | 3' | 4'-CH$_3$ |
| 12 | 3' | 4'-OCH$_3$ |
| 13 | 3' | 4'-OC$_2$H$_5$ |
| 14 | 4' | 3'-OCH$_3$ |
| 15 | 4' | 2',5'-OCH$_3$ |

EXAMPLES 16-21

The method of Example 9 is used to prepare the corresponding benzothiazole-5-carboxylic acids:

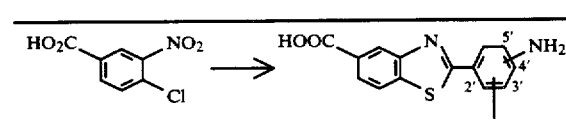

| Example | NH$_2$ | R |
|---|---|---|
| 16 | 4' | 3'-CH$_3$ |
| 17 | 3' | 4'-CH$_3$ |
| 18 | 3' | 4'-OCH$_3$ |
| 19 | 3' | 4'-OC$_2$H$_5$ |
| 20 | 4' | 3'-OCH$_3$ |
| 21 | 4' | 2',5'-OCH$_3$ |

EXAMPLES 22-36

The method of Example 7 is used to prepare the following compounds:

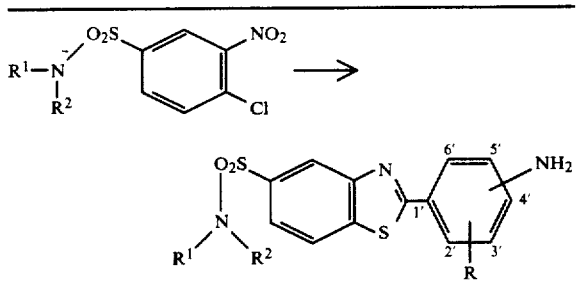

| Example | NH$_2$ | R | R$^1$ | R$^2$ |
|---|---|---|---|---|
| 22 | 4' | H | H | H |
| 23 | 4' | H | H | CH$_3$ |
| 24 | 4' | H | CH$_3$ | CH$_3$ |
| 25 | 3' | H | H | H |
| 26 | 4' | H | H | 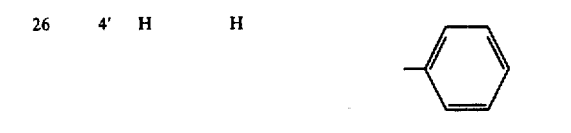 |
| 27 | 4' | 3'-CH$_3$ | H | 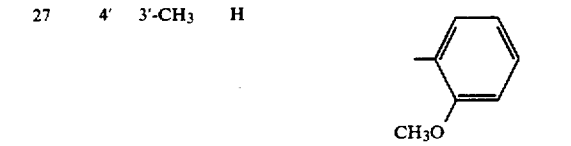 |
| 28 | 4' | 3'-OCH$_3$ | | —C$_2$H$_4$—O—C$_2$H$_4$— |
| 29 | 4' | H | H | 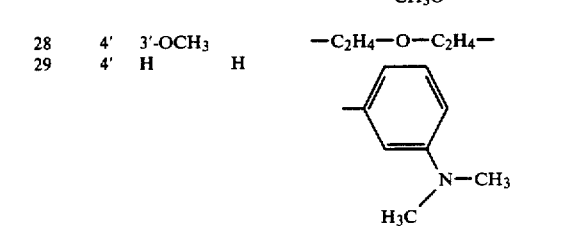 |
| 30 | 4' | H | H | 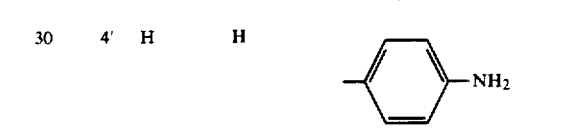 |
| 31 | 4' | H | H | 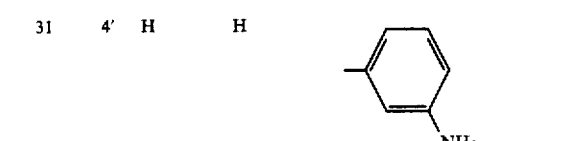 |
| 32 | 4' | H | R$^1$ + R$^2$ = | 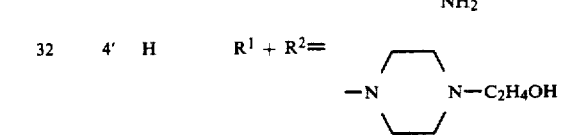 |
| 33 | 4' | H | | —C$_2$H$_4$—O—C$_2$H$_4$— |
| 34 | 3' | 4'-OCH$_3$ | CH$_3$ | —CH$_3$ |
| 35 | 3' | 4'-CH$_3$ | H | 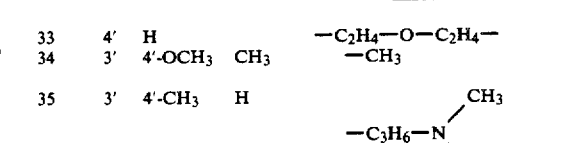 |
| 36 | 3' | 4'-OCH$_3$ | R$^1$=R$^2$= | —C$_2$H$_4$OCH$_3$ |
| 37 | 4' | H | H | —SO$_2$CH$_3$ |

-continued

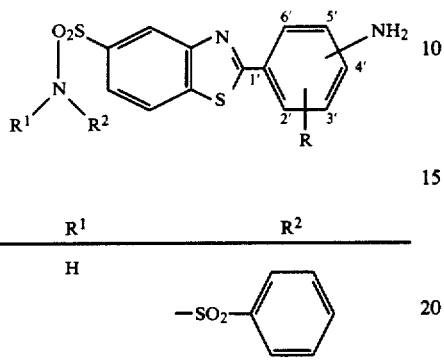

| Example | NH₂ | R | R¹ | R² |
|---|---|---|---|---|
| 38 | 4' | H | H | —SO₂—C₆H₅ |

EXAMPLES 39–52

Analogous 4-chloro-3-nitrobenzenecarboxamides are used analogously to Examples 22–39 to prepare the corresponding 2-(aminophenyl)-benzothiazole-5-carboxamides.

We claim:

1. A benzothiazole derivative of the formula

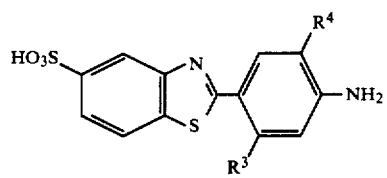

wherein
$R^3$ = H, CH₃, OCH₃, OC₂H₅, Cl
$R^4$ = H, CH₃, OCH₃, OC₂H₅, Cl.

2. A benzothiazole derivative according to claim 1 wherein $R^3$ and $R^4$ = hydrogen.

* * * * *

UNITED STATES PATENT AND TRADEMARK OFFICE
CERTIFICATE OF CORRECTION

PATENT NO. : 4,705,861

DATED : Nov. 10, 1987

INVENTOR(S) : Fürstenwerth et al.

It is certified that error appears in the above-identified patent and that said Letters Patent is hereby corrected as shown below:

| | |
|---|---|
| Col. 2, line 55 | Delete "R" in the first instance and substitute --A-- |
| Col. 3, line 50 | Correct spelling of --trichloroethane-- |
| Col. 5, line 11 | Correct spelling of --aminothiophenols-- |

Signed and Sealed this

Fourteenth Day of June, 1988

Attest:

DONALD J. QUIGG

Attesting Officer

Commissioner of Patents and Trademarks